United States Patent
Gerrans (10) Patent No.: US 10,194,799 B2
(45) Date of Patent: Feb. 5, 2019

(54) ROBOTIC OPHTHALMOLOGY

(71) Applicant: Lawrence J. Gerrans, San Anselmo, CA (US)

(72) Inventor: Lawrence J. Gerrans, San Anselmo, CA (US)

(73) Assignee: Sanovas Intellectual Property, LLC, Reno, NV (US)

(*) Notice: Subject to any disclaimer, the term of this patent is extended or adjusted under 35 U.S.C. 154(b) by 0 days.

(21) Appl. No.: 14/642,221

(22) Filed: Mar. 9, 2015

(65) Prior Publication Data
US 2016/0262617 A1 Sep. 15, 2016

(51) Int. Cl.
| | |
|---|---|
| *A61B 3/10* | (2006.01) |
| *A61B 3/14* | (2006.01) |
| *A61B 3/02* | (2006.01) |
| *A61B 3/00* | (2006.01) |
| *A61B 3/18* | (2006.01) |
| *A61B 3/113* | (2006.01) |
| *B33Y 50/00* | (2015.01) |
| *A61B 3/028* | (2006.01) |
| *A61B 3/103* | (2006.01) |
| *B29D 12/02* | (2006.01) |
| *B33Y 10/00* | (2015.01) |
| *B33Y 30/00* | (2015.01) |
| *B33Y 80/00* | (2015.01) |
| *A61B 3/032* | (2006.01) |

(Continued)

(52) U.S. Cl.
CPC .............. *A61B 3/18* (2013.01); *A61B 3/0058* (2013.01); *A61B 3/0083* (2013.01); *A61B 3/028* (2013.01); *A61B 3/103* (2013.01); *A61B 3/113* (2013.01); *B29D 12/02* (2013.01); *B33Y 50/00* (2014.12); *A61B 3/0025* (2013.01); *A61B 3/0075* (2013.01); *A61B 3/032* (2013.01); *A61B 3/036* (2013.01); *A61B 3/14* (2013.01); *A61F 2/141* (2013.01); *B33Y 10/00* (2014.12); *B33Y 30/00* (2014.12); *B33Y 80/00* (2014.12); *G02C 11/10* (2013.01)

(58) Field of Classification Search
CPC ........ G02C 13/005; G02C 5/00; A61B 3/103; A61B 3/14; A61B 3/113; A61B 3/1225; A61B 3/024; A61B 3/032; A61B 3/1015
USPC ................ 351/204, 200, 205–206, 209–210, 351/221–223, 41, 246
See application file for complete search history.

(56) References Cited

U.S. PATENT DOCUMENTS

| 4,869,589 A | 9/1989 | Blair et al. | |
|---|---|---|---|
| 5,841,502 A * | 11/1998 | Miwa ..................... | A61B 3/152 351/209 |

(Continued)

FOREIGN PATENT DOCUMENTS

WO WO 2013149891 A1 * 10/2013 ......... B29C 67/0059

*Primary Examiner* — Dawayne A Pinkney
(74) *Attorney, Agent, or Firm* — Forge IP, PLLC (57) ABSTRACT

A robotic vision screening system includes a user interface that interacts with a customer, at least one diagnostic device that examines at least one of the customer's eyes, at least one measurement device that measures the customer's head anatomy, a processor in communication with the at least one diagnostic device and the at least one measurement device, and a 3D printer in communication with the processor that produces a customized vision correction device based on data received from the at least one diagnostic device and the at least one measurement device.

25 Claims, 5 Drawing Sheets

(51) Int. Cl.
  *A61B 3/036* (2006.01)
  *G02C 11/00* (2006.01)
  *A61F 2/14* (2006.01)

(56) References Cited

U.S. PATENT DOCUMENTS

| | | |
|---|---|---|
| 6,003,991 A | 12/1999 | Viirre |
| 6,027,217 A | 2/2000 | McClure et al. |
| 6,238,049 B1 | 5/2001 | Griffin et al. |
| 6,386,707 B1 | 5/2002 | Pellicano |
| 7,384,146 B2 | 6/2008 | Covannon et al. |
| 7,520,611 B2 | 4/2009 | Franz et al. |
| 7,614,747 B2 | 11/2009 | Foster |
| 7,860,594 B2 | 12/2010 | Andino et al. |
| 8,182,091 B2 | 5/2012 | Foster |
| 8,740,386 B2 | 6/2014 | Foster |
| 2007/0073113 A1 | 3/2007 | Squilla et al. |
| 2007/0091264 A1* | 4/2007 | Kahlen ................. A61B 3/113 351/206 |
| 2008/0062381 A1* | 3/2008 | Doshi .............. B29D 11/00028 351/159.69 |
| 2008/0189173 A1 | 8/2008 | Bakar et al. |
| 2010/0183205 A1* | 7/2010 | Pfleger .................. A61B 3/113 382/128 |
| 2013/0141694 A1 | 6/2013 | Seriani |
| 2014/0129259 A1 | 5/2014 | Seriani |
| 2014/0184496 A1* | 7/2014 | Gribetz ................ G02B 27/017 345/156 |
| 2014/0192327 A1 | 7/2014 | Sindt et al. |
| 2014/0218682 A1 | 8/2014 | Foster |
| 2014/0268060 A1* | 9/2014 | Lee ..................... A61B 3/0041 351/241 |
| 2015/0055085 A1* | 2/2015 | Fonte ................ G06Q 30/0621 351/178 |

* cited by examiner

ROBOTIC OPHTHALMOLOGY

FIELD OF THE INVENTION

The present invention relates to systems and methods for visualizing eye anatomy for diagnostic and therapeutic purposes. More specifically, the present invention relates to a robotic visual screening system that is capable of performing a variety of diagnostic and therapeutic tests and creating a highly customized eye vision correction device.

BACKGROUND OF THE INVENTION

Almost every person at some point in their life requires some form of vision correction. In addition, many people will require more advanced eye tests to diagnose various more serious medical conditions, such as glaucoma, retinal disease, cataracts, etc.

In most countries, including the Unites States, in order to get a pair of glasses or contact lenses, a person needs to obtain a prescription from a licensed optometrist or ophthalmologist. Therefore, a person is required to make an appointment with the physician and visit the physician's office for a vision or other tests. This can be inconvenient if someone lives in a remote area and has to travel for a long time to get to the physician's office. Additionally, physician's office visits can be costly because they have to cover the physician's time spent with the patient, as well as other business expenses. Furthermore, because many patient's prefer to obtain or require a vision correction device on the spot, many physicians have to carry a large inventory of eye glasses and/or contact lenses to be dispensed to the patient, which can be inconvenient and costly for the physician. If the patient prefers a highly customized pair of glasses or contact lenses, he or she typically has to go to a specialty store to order them and then wait for a few weeks for them to be ready for pick up.

There are a number of prior art systems that attempt to solve the problems associated with a typical physician visit. For example, U.S. Pat. No. 8,740,386 to Foster discloses an automated vision screening system that performs various visual acuity tests, Snellen test, Landolt C test, glaucoma tests, color vision deficiency tests, and refractive error test. The system provides result reports at the kiosk or via the Internet to a third party, e.g. physician or lens supplier. The system can provide referrals, schedule appointments, request and collect payments from users, and dispense plano lenses. The system provides visual, physical and audio communication means and includes an eye cup for the patient to place their eye next to.

U.S. Pat. No. 7,384,146 to Covannon et al. discloses an automated diagnostic eye examination and fulfillment system. The system prompts the user to enter personal information and method of payment. Then, the user is instructed through various visual and diagnostic tests. The test data is analyzed and a report/prescription is generated for the user. The system may also create and dispense pre-selected prescription glasses to the user.

U.S. Pat. No. 7,520,611 to Franz et al. discloses an optical telemedicine system including an examination location, a diagnostic location and a telecommunication link for transmittal of test data from the examination location to the diagnostic location for rendering a diagnosis. The patient can examine himself or with a help of a technician. The diagnosis report may be transmitted back to the examination center to be printed for the patient's records. The patient's information may be entered via keyboard, voice command or touch screen. The system may also utilize a video conference device for remote communication with the diagnostic location.

However, the above-discussed prior art systems still suffer from a number of drawbacks. For example, these systems do not automatically analyze the test data at the location and render a diagnosis/prescription to the patient on the spot. Additionally, the prior art systems are not capable of creating a customized pair of eye glasses or contact lenses via 3-D printing to be dispensed to a customer on the spot. Furthermore, these systems do not include a capability of measuring a person's face and/or head anatomy to allow the customer to visualize how a vision correction device looks on them before deciding to purchase it and to produce a highly customized vision correction device on the spot that is based on a model of each customer's head/face anatomy.

Therefore, it is an objective of this invention to create a fully or at least partially automated very comprehensive eye test and measurement system that also has a point-of-purchase capability where a customer may obtain a highly customized eyewear product on the spot. The system of the present invention provides an advantage in that optometrists and ophthalmologists would no longer have to carry a large inventory of lenses and glasses to accommodate the patient's need. Instead, customized glasses or lenses may be prepared on the spot by the system of the present invention. Another objective of the present invention is to create various types of unconventional clinical eyewear that is geared towards each patient's unique anatomy and needs.

SUMMARY OF THE INVENTION

In order to overcome the deficiencies of the prior art and to achieve at least some of the objects and advantages listed, the invention comprises a robotic vision screening system, including a user interface that interacts with a customer, at least one diagnostic device that examines at least one of the customer's eyes, at least one measurement device that measures the customer's head anatomy, a processor in communication with the at least one diagnostic device and the at least one measurement device, and a 3D printer in communication with the processor that produces a customized vision correction device based on data received from the at least one diagnostic device and the at least one measurement device. In some embodiments, the customized eye vision correction device comprises eye glasses. In additional embodiments, the customized eye vision correction device comprises contact lenses. In further embodiments, the customized eye vision correction device comprises an artificial eye.

In some embodiments, the at least one measurement device is a laser scanning device.

In certain embodiments, the at least one measurement device measures at least one of a head measurement, a brow measurement, an eye measurement, an ear measurement, a nose measurement, and a cheek measurement.

In some embodiments, the processor creates a 3D model of the customer's head based on the measurements received from the at least one measurement device. In certain of these embodiments, the system further includes a display, wherein the display displays the 3D model of the customer's head to the customer. In some of these embodiments, the system further includes a menu of vision correction devices selectable by the customer, wherein the menu includes at least one of a style, color, size and dimension. In additional of these embodiments, the display displays a vision correction device selected by the customer together with the 3D model of the customer's head. In further of these embodiments, the 3D printer produces a vision correction device that is customized based on the customer's input from the menu.

In certain embodiments, the at least one diagnostic device includes at least one camera for visualizing eye anatomy using a visible light spectrum and an invisible light spectrum.

In some cases, the system further includes a communication link that communicates with a remotely positioned provider.

In certain embodiments, the system also includes a reporting device that issues an examination report and/or a prescription.

In some embodiments, the 3D printer is configured to print vision correction devices that allow the customer to see different light spectra.

A method for robotic vision screening is also provided, including the steps of providing a user interface for interaction with a customer, examining at least one of a customer's eyes via at least one diagnostic device, measuring the customer's head anatomy via at least one measurement device, processing data obtained by the at least one diagnostic device and the at least one measurement device via a processor, and producing a customized vision correction device via a 3D printer based on the processed data and dispensing the device to the customer.

In some embodiments, the customized eye vision correction device includes eye glasses. In additional embodiments, the customized eye vision correction device includes contact lenses. In further embodiments, the customized eye vision correction device comprises an artificial eye.

In some cases, the customer's head anatomy is measured via a laser scanning device.

In some embodiments, the method further includes the steps of creating a 3D model of the customer's head based on the measurements received from the at least one measurement device and displaying the 3D model of the customer's head to the customer via a display.

In some embodiments, the step of producing the customized vision correction device includes producing a vision correction device having a first microcamera and a second microcamera, wherein the first microcamera is configured to visualize a wearer's eye, and the second microcamera is configured to visualize the wearer's surroundings, such that the first and second microcameras produce an image of what the wearer sees when wearing the device.

In certain embodiments, the method further includes the step of measuring movement of the customer's eyes via the at least one measurement device and adjusting positioning of the at least one diagnostic device in relation to the eyes based at least in part of the measured movement.

Other objects of the invention and its particular features and advantages will become more apparent from consideration of the following drawings and accompanying detailed description.

DETAILED DESCRIPTION OF THE INVENTION

Figure 1:
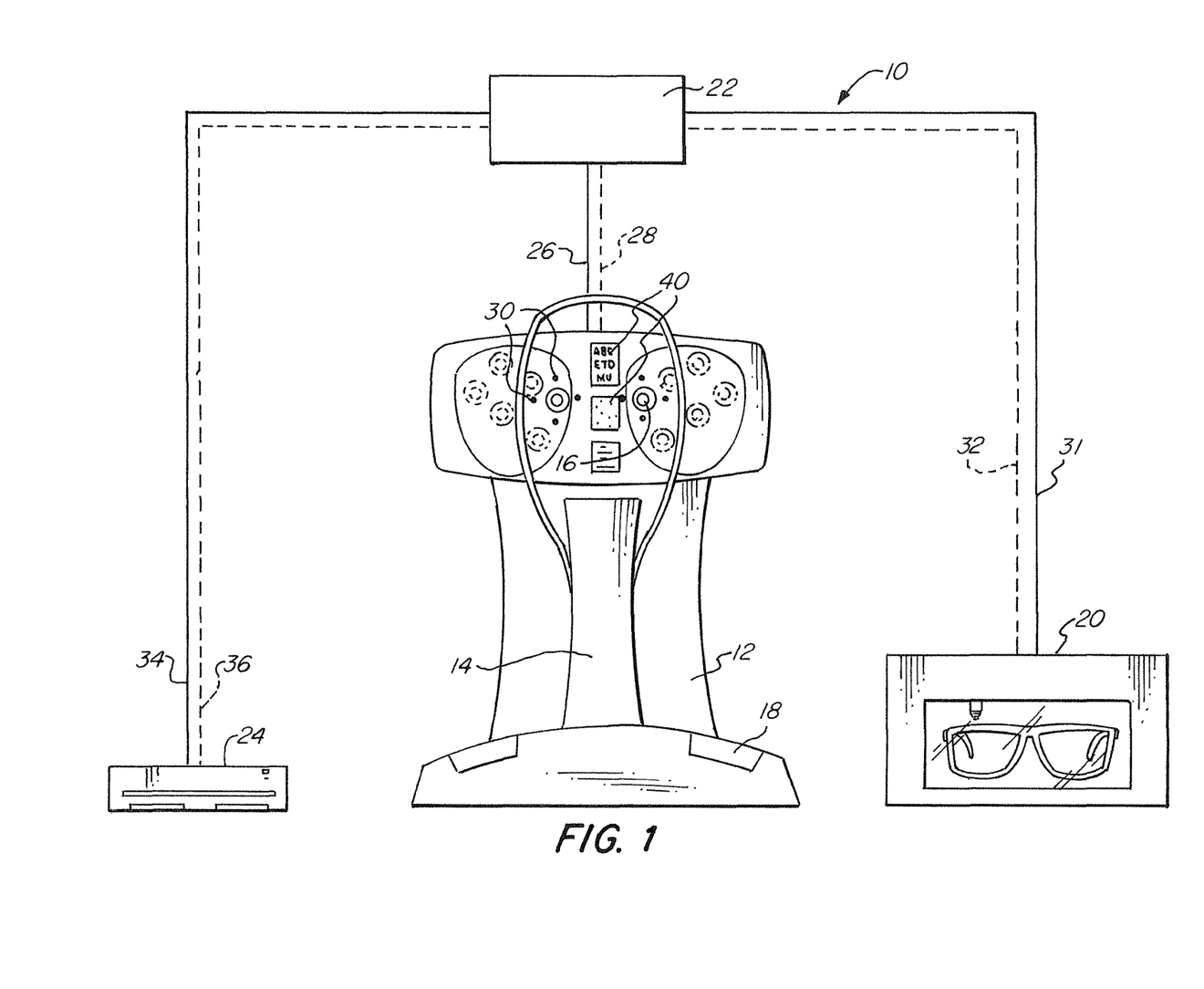
FIG. 1 is a partially schematic view of the robotic vision screening system of the present invention.

The basic components of one exemplary embodiment of a robotic vision screening system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The robotic vision screening system (10) of the present invention, as shown in FIG. 1, has a housing (12) that includes various components of the system, as described in more detail below. In one exemplary embodiment shown in this figure, the housing is a standalone unit that can be placed on any flat surface or can have a support unit for placement of the housing on the floor. The housing (12) includes a positioning device (14) for positioning a person's head in correct position for performing a variety of tests. The positioning device may include a chin rest and a forehead rest or similar structures to position and align a person's head. It is understood that any other suitable housing design may be used in accordance with the present invention.

The housing (12) further includes one or more diagnostic devices that examine at least one of the person's eyes. In some embodiments, the diagnostic devices comprise at least one camera (16) for visualizing the person's eye anatomy. In the embodiment shown in FIG. 1, the housing includes two cameras, one for visualizing the anatomy of each eye. It is understood that only one camera may also be provided. It is further understood that in some embodiments, two or more cameras may be provided to visualize the anatomy of each eye.

The cameras (16) may comprise any imaging device suitable for viewing the target area, such as a coherent fiber bundle or appropriate optical element and lens assembly in conjunction with an imaging sensor (e.g., CMOS, CCD), having a sufficiently small outer diameter, preferably about 0.75 mm-2.5 mm, and more preferably about 1 mm or less.

The housing further includes one or more illumination devices (30) positioned adjacent the cameras (16). The illumination devices may be LEDs, lasers, fiber optic cables, or any other suitable illumination device. The illumination devices (30) emit various types of light, depending on the desired application. For example, the illumination devices (30) may emit ambient light, visible spectrum light, ultraviolet light, infrared light, near infrared light, etc.

Any desirable configurations of the cameras (16) and the illumination devices (30) may be provided in accordance with the present invention. Some exemplary configurations are shown in FIGS. 3A-3F. In the embodiments illustrated in these figures, two, three, or four cameras (16) may be used to image a single eye. The cameras (16) may be positioned in any desirable configuration, such as in line or in a shape of a triangle or a square. One, two, three, four or five illumination devices (30) may be used together with any number and configuration of the cameras (16), and the illumination devices (30) may be have any desirable orientation with respect to the cameras. When multiple cameras are provided to visualize each eye, the cameras may move as a unit or each camera may be actuated separately to visualize the eye at a different view angle. It is noted that the numbers and configurations of the cameras and illumination devices shown in these figures are only exemplary, and that any other number and/or arrangement of the cameras and illumination devices may be used in accordance with the present invention.

The system of the present invention may utilize any of the systems and methods for visualization of eye anatomy described in U.S. application Ser. No. 14/582,716 and U.S. application Ser. No. 14/481,254, the disclosure of which is incorporated by reference herein in its entirety.

In addition to having one or more cameras (16) for visualizing the eye anatomy, the housing may include a variety of other diagnostic devices. As shown in FIG. 1, in some embodiments, the housing includes vision charts (40) placed in front of the person's eyes. The charts display letters/numbers/symbols of various sizes to the person being tested to determine the strength of the person's vision. In additional embodiments, the housing also includes a phoropter device that switches multiple lenses in front of the person's eyes to determine refraction, i.e. exactly how a lens must be shaped and curved to correct the person's vision to a normal state. This device is useful when a person has a vision problem such as nearsightedness, farsightedness or astigmatism. Any other desirable diagnostic device may also be used in accordance with the present invention.

Figure 2:
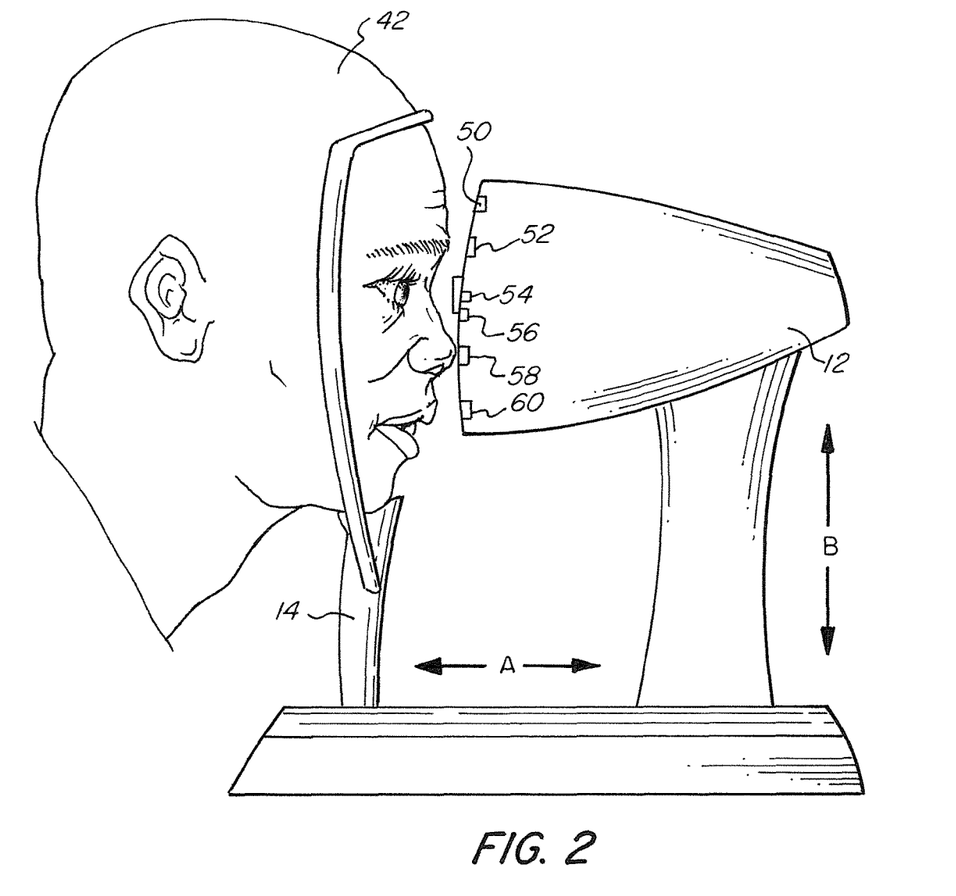
FIG. 2 is a side view of a housing of the robotic vision screening system of FIG. 1.
Figure 3A:
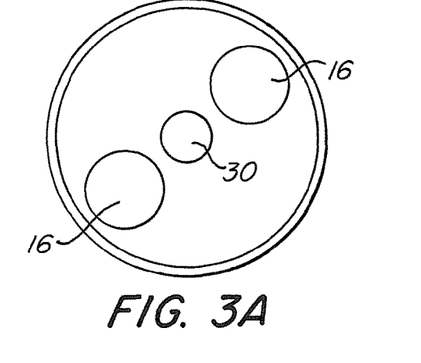
FIGS. 3A-3F are pupil views of various configurations of cameras and illumination devices of the robotic vision screening system of FIG. 1.
Figure 3B:
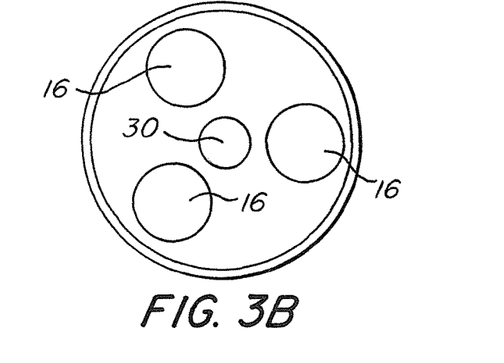
Figure 3C:
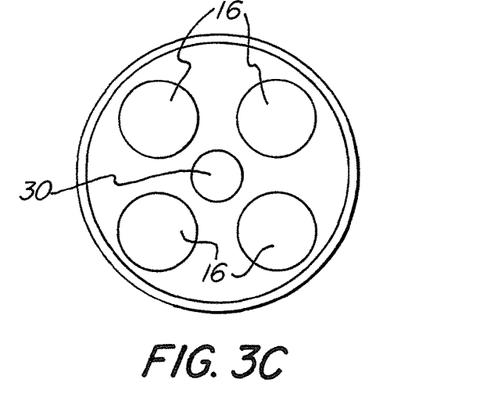
Figure 3D:
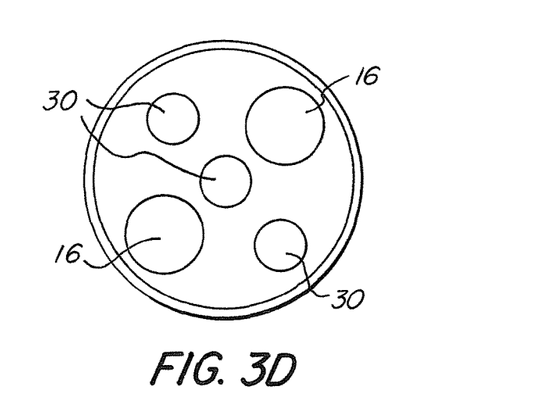
Figure 3E:
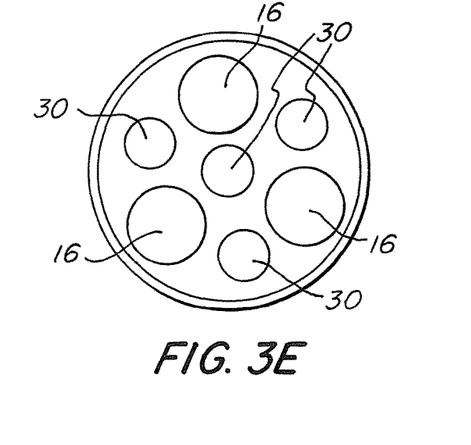
Figure 3F:
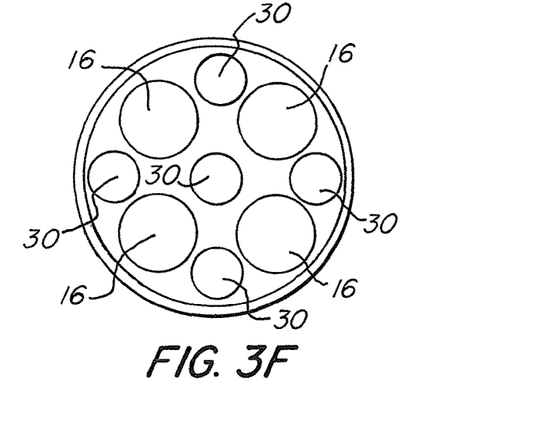

As shown in FIG. 2, the top portion of the housing (12) with the cameras (16) and/or other diagnostic devices is movable in a direction toward and away from the person's head (42), as well as in a vertical up and down direction with respect to the person's head (42). When in use, once the person's head is positioned in the chin rest and the forehead rest, the diagnostic devices and various measurement devices described below may be positioned at a desired distance from the person's eye(s) and/or face by actuating the housing (12) in the directions shown with arrows A and B.

The cameras (16) are coupled to one or more actuators that enable a linear and/or rotational movement of the cameras to provide a larger angle of view of the eye anatomy. Any suitable actuator may be used to actuate the cameras. Once the housing (12) is positioned at a desired distance from the eye(s), the cameras (16) are actuated in directions substantially parallel to the vertical and horizontal axes of the eye to get a wide angle view of the eye anatomy. The actuation is controlled by a processor that communicates with the cameras, as discussed below. While the cameras (16) are being actuated, the chin rest and the forehead rest remain stationary to maintain the person's head and eye(s) in the same position. If two or more cameras are provided, each of the cameras may move separately from the other cameras, or the two or more cameras may move together as a unit.

In some advantageous embodiments, a screen may be provided between the cameras (16) and the person's eye(s). A static and/or dynamic image is shown on the screen and the person is asked to focus on the image while the cameras (16) move around to capture images of the eye anatomy. Once the image data is captured by the cameras, it is sent to the processor for processing and analysis, as described in more detail below.

The system of the present invention allows examination of the eye anatomy using light of various spectrums and various wavelengths. This allows for detection, visualization and characterization of various tissues, structures, and molecular compounds that may be present in the eye, which in turn lead to diagnosis of various eye and body diseases. This is due to the fact that various tissues and structures that may be present in the eye absorb and/or deflect light of various spectrum and/or wavelengths in different ways. Analysis of the light scattering thereby provides information about particular tissues and structures present in the eye. The system of the present invention also allows for detection and characterization of changes in eye anatomy over time, which may be caused by various diseases. The system is capable of measuring color saturation of the light emitted onto the target tissues and also measures scattering of light deflected from the target tissues in the eye.

As noted above, the system of the present invention may utilize a plurality of illumination devices or light sources. In some embodiments, all of the light sources emit light of the same spectrum/wavelength. In additional embodiments, each of the plurality of light sources emits light of a different spectrum/wavelength than the light emitted by other light sources. This allows for detection and characterization of various structures and conditions inside the eye, as described above.

In some advantageous embodiments, the system of the present invention utilizes a continuous wave/stream of light. In other advantageous embodiments, the system uses a pulsed light, wherein the light emitting devices positioned on the system adjacent the cameras emit pulses of light at a desired frequency. The cameras may capture image data after each pulse of light, or at particular intervals after a certain number of light pulses. In further advantageous embodiments, the same light sources may emit light in both continuous wave and pulsed waves, as desired, and/or some of the light sources may emit light continuously and other light sources may emit light in pulsed waves.

Referring back to FIG. 1, the system (10) further includes a processor (22) coupled to one or more cameras (16) for receiving and processing image data captured by the cameras. The processor (22) similarly receives and processes data collected by any other diagnostic device of the system (10). Any suitable processor may be used in accordance with the present invention. For example, the processor (22) may be a personal computer. The digital image data captured by the cameras (16) is transmitted to the processor for analysis. One of the techniques that may be utilized to process the captured digital data is spectroscopy, which analyzes interaction between matter and radiated energy. By utilizing spectroscopy techniques, it is possible to digitally process spectrums and wavelengths reflected from the eye to detect and characterize various elements present in the eye.

In one advantageous embodiment, the processor (22) is connected to the cameras (16) and/or other diagnostic devices via a cable or wired connection (26). In additional advantageous embodiments, the processor (22) is connected to the cameras (16) and/or other diagnostic devices via a wireless, e.g. cellular or satellite, connection (28), which is desirable if the processor needs to be positioned remotely from the person whose eye anatomy is being examined. Furthermore, the cameras (16), other diagnostic devices and/or the processor (22) may be connected to an external storage device, a removable storage device, and/or to an internet port. The data captured by the cameras and/or other diagnostic devices is stored on the storage device and may be later retrieved by the customer and/or physician. In other advantageous embodiments, the processor (22) may have an internal storage device. Any suitable storage device may be used in accordance with the present invention.

In some embodiments, the image data is compressed before it is transmitted to the processor for processing or stored. In other words, the imaging data is encoded using fewer bits than the originally captured data to reduce resource usage, such as data storage space or transmission capacity. Once the compressed data is received by the processor, it is decompressed before it is displayed to the user to maintain the original quality of the captured images.

The system (10) further includes a user interface (18). The user interface may be integral with the housing (12) or may be a separate unit in communication with the diagnostic devices positioned in the housing and/or the processor (22). In some embodiments, the user interface (18) is an audio interface which interacts with the user via voice commands. In additional embodiments, the user interface (18) is a visual interface that interacts with the user via visual commands. For example, the user interface may be a screen provided with the system (10) that displays various commands to the user or an overlay image provided on the screen positioned between the cameras (16) and the person's eye(s), as described above. In further embodiments, the user interface (18) is a manual interface that includes at least one of a keyboard, a touchscreen, or a direct manipulation interface. It is understood that the user interface (18) may include any other suitable device that allows a user to input information and commands. The user interface is connected to the processor via a cable connection or via a wireless connection.

As shown in FIG. 2, the housing (12) also includes at least one measurement device that measures the person's face and/or head anatomy. Any suitable type of the measurement device may be used in accordance with the present invention. In some embodiments, the measurement device is a laser scanning device. The measurement device may include a head measurement device (50) that measures the dimensions of the person's head, a brow measurement device (52) that measures the distance between the person's brows, as well as the distance between the brows and other facial features, and an eye measurement device (54) that measures the position of the eyes and the distance between the eyes. The measurement device may further include an ear measurement device (56) that measures the distance from the eyes and nose to the ears, a nose measurement device (58) that determines the position of the nose relative to other facial features, and a cheek measurement device (60) that measures the anatomy of the cheek bones.

Figure 4:
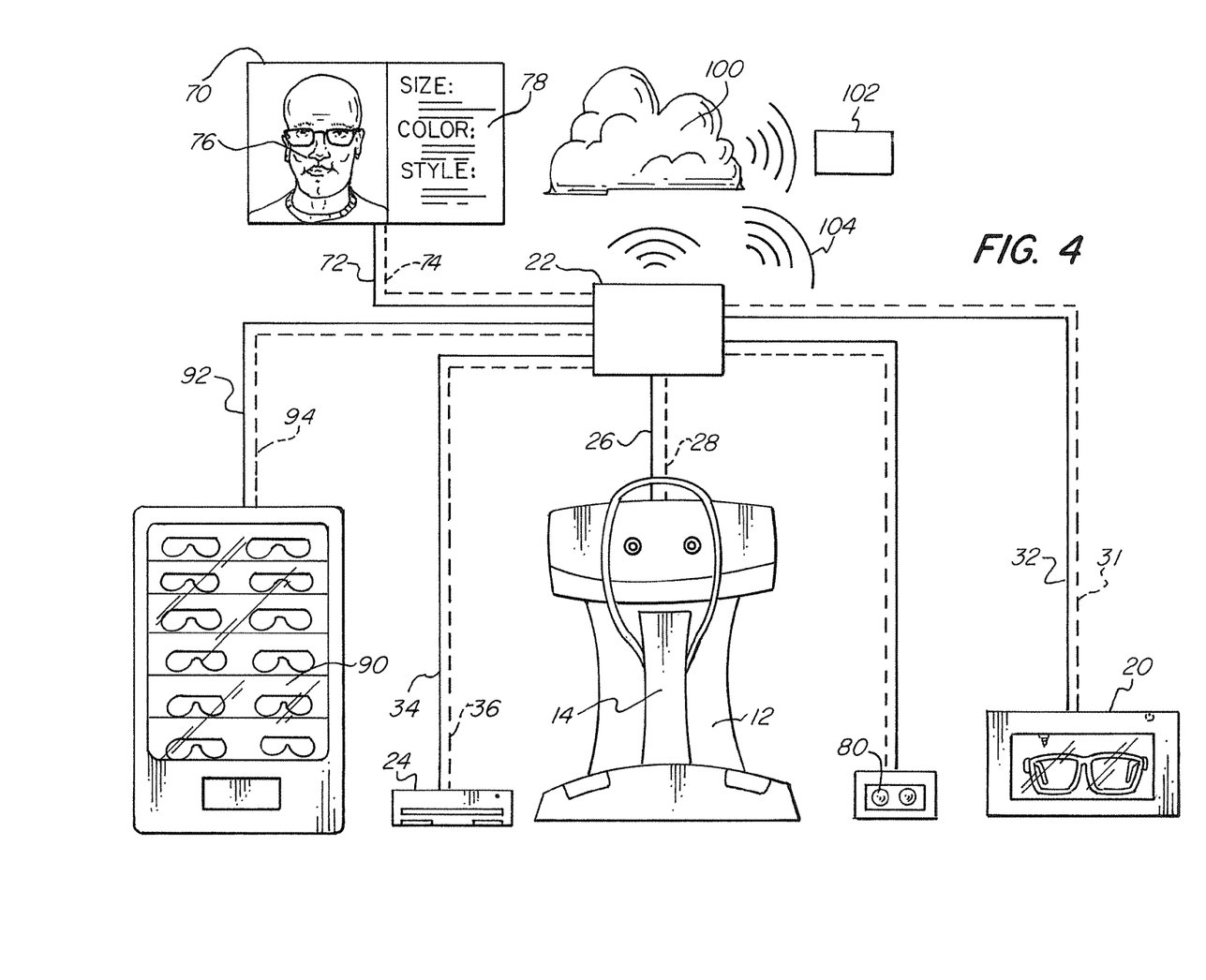
FIG. 4 is another partially schematic view of the robotic vision screening system of the present invention.

The measurement devices are connected to the processor (22) via a wired or a wireless connection. The processor receives and analyzes data from the measurement devices and creates a 2D and/or 3D model of the person's head and/or face based on the received measurements. As shown in FIG. 4, the system (10) may further include a display (70) that displays the model of the person's head (76). The display (70) is connected to the processor (22) via a wired connection (72) or a wireless connection (74). The display (70) may be integral with the housing (12) or may be a standalone unit placed in proximity to the housing (12).

The system (10) also includes a menu of vision correction devices, e.g. eye glasses or contact lenses, selectable by the user. In some advantageous embodiments, as shown in FIG. 4, the menu (78) is displayed to the user on the display (70). The menu may include at least one of a style, color or size, or any other desirable characteristics of the vision correction device, such as dimension (i.e. distance between the lenses and width of lenses). For example, where the desired vision correction device is eye glasses, the customer may select the style, color and size of the glasses from the menu (78) to create highly customized eyewear. The selected eyewear is then displayed to the customer on the display (70) together with the model of the customer's head (76), such that the customer can visualize how the eyewear will look on his or her face. If the customer is not satisfied with the selected eyewear, he or she can choose another style, color or size from the menu and visualize the newly selected eyewear on the display (70) together with the model of the customer's head. The same process is also utilized for selection of contact lens color. This way, the system of the present invention provides a real-time image of what the eye glasses or contact lenses would look like on the wearer's head/face before the wearer decides to purchase them.

The ability to choose dimension of the vision correction device allows the customer to eliminate a refractive glare when wearing a vision correction device. Additionally, the data collected by the measurement devices may be used to modify a person's prescription to create a spherical lens consistent with the person's face anatomy to create a lens that improves peripheral vision.

Once the customer is satisfied with the design of the vision correction device chosen, he or she confirms the selection via the user interface. The system (10) than uses the data from the diagnostic devices, the measurement devices and the input by the customer to create a highly customized vision correction device.

In some embodiments, the measurement devices (50, 52, 54, 56, 58, 60) include one or more motion sensors that can sense and measure movement of the customer's eye in relation to the diagnostic devices in real time. These measurements are then transmitted to the processor (22), which processes the data and adjusts positioning of the diagnostic devices vis-à-vis the eyes to eliminate movement artifacts when performing the diagnostic tests. The measurement devices can also detect and measure blinking of eyelashes and the processor adjusts the test results to account for the blinking.

As shown in FIGS. 1 and 4, the system (10) further includes a 3D printer (20) in communication with the processor (22). Any type of 3D printer known in the art may be used in accordance with the present invention. The printer (20) is connected to the processor via a wired connection (31) or a wireless connection (32). The printer may be positioned in the vicinity of the housing (12) or may be placed at a remote location. The 3D printer receives data from the processor (22) regarding the customer's eye vision, selected eyewear design and the measurements of the customer's face and head anatomy. This data is used by the printer to print a highly customized vision correction device.

In some embodiments, the 3D printer produces the entire glasses, including a frame and lenses that fit into the frame. In other embodiments, only lenses are printed on the 3D printer. The lenses are then fitted into prefabricated frames and dispenses to the customer. The customer may be presented with a menu of available prefabricated frames for selection and viewing of the frames on the display together with the model of the customer's face/head.

In some embodiments, the device, e.g. glasses or contact lenses, are printed right on the spot to be dispensed to the customer. In other embodiments, the system sends the measured head/face anatomy characteristics, eyesight prescription, and the customer's preferences to a remote location that will then manufacture eyewear and mail it to the customer. It is noted that the system (10) of the present invention may include one of the 3D eyeglasses printer (20), 3D contact lenses printer (80) or both, as shown in FIG. 4.

In additional embodiments, as illustrated in FIG. 4, the system (10) also includes a vision correction device dispensing station (90). The station may be positioned in the vicinity of the housing (12), or may be located remotely. The station (90) contains a selection of eye glasses and/or contact lenses of different prescription strength, styles, sizes and colors. The dispensing station is connected to the processor (22) via a wired (92) or a wireless (94) connection. In this embodiment, the customer may be presented with a preset menu of various available styles of eye glasses and/or contact lenses. The customer may then select a pair of eye glasses or contact lenses and view the real time image of what they would look like on the customer's head/face via the display (70). Once the customer selects the eyewear that he or she likes, via the user interface (18), this information is sent to the dispensing station (90) for dispensing the chosen eyewear to the customer.

The system (10) further includes a reporting device (24), as illustrated in FIGS. 1 and 4. The reporting device may be a conventional printer or any other suitable device. The reporting device (24) may be positioned in proximity to the housing (12) or at a remote location and may be connected to the processor (22) via a wired connection (34) or a wireless connection (36). The reporting device is utilized to issue an examination report, a vision correction device or medication prescription, a sales receipt, etc. to the customer.

The system (10) may also include a communication link (104) that communicates with a remotely positioned physician (102). The communications link provides connection between the processor (22) and other components of the system (10) and a receiving device from which the physician can obtain various information from the system (10). The receiving device may be a personal computer, a hospital or clinic patient management system, a mobile device, or any other suitable device. The communications link (104) sends various data obtained by the system, such as results of various vision and ophthalmic tests performed on the customer, to the physician (102). The physician can then review and analyze the data and send back a report, diagnosis and/or prescription for a vision correction device or medication to be presented to the customer.

The system (10) can also communicate with various other entities. For example, the system can communicate with medical insurance companies to transmit and receive information regarding a customer's medical insurance coverage for a particular test or vision correction device. In additional embodiments, the system may communicate with a financial institution, e.g. a bank, to process payment information from the customer. Furthermore, in the embodiments where the vision correction device is not produced on the spot, the system may communicate with a manufacturer of the vision correction device to send information regarding the customer's selection of eyewear to be produced by the manufacturer. It is understood that the system (10) may communicate with any other entities, as desired.

In further embodiments, the data captured by the system (10) may be stored in cloud storage (100), meaning that the digital data is stored in logical pools, with the physical storage typically spanning across multiple servers managed by a hosting company. This way, the data may be easily accessed from any location connected to the cloud storage, such as physicians' and customers' personal computers, tablets and smart phones.

The system of the present invention is a fully or at least partially automated system that walks a patient through various standard eye exam tests. The system may also perform various more advanced eye tests typically performed by ophthalmologists. The system is capable of issuing test results and/or diagnosis in real time and producing a highly customized eyewear product on the spot. The system of the present invention may be placed in optometrists or ophthalmologists offices, or in any public place, such as a supermarket or pharmacy.

When in use, a customer first initiates interaction with the system (10) via the user interface (18). The customer will be presented with a menu of available eye test procedures. Once the customer selects the procedure, the system (10) will walk the customer through the steps necessary for the procedure via the user interface. For example, for a standard eye vision test, the customer may be instructed to place their chin and/or forehead in the chin rest/forehead rest (14) provided in the housing (12). Then, the customer may be instructed to look at various vision test charts (40) and verbally or manually input the information about what is shown in the charts. The system may also use a phoropter to determine whether the person has nearsightedness, farsightedness or astigmatism.

Once the selected eye test is complete, the system will notify the customer and present further choices for selection by the customer. For example, if the customer desires to purchase a vision correction device, the system will also utilize various measurement devices to determine the anatomy of the customer's face/head to create a model of the customer's head/face, which is then displayed to the customer on the display (70). The customer can select the style, size and/or color of eye wear, see how the selected eyewear looks on the customer on the display and then make a final selection of the eyewear through the user interface. The selection is then sent to the processor (22), together with the customer's eye vision prescription information to be communicated to the 3D printer or the manufacturer for producing the selected eyewear.

The system may also communicate the test results to a remotely positioned physician for confirmation of the diagnosis and issuance of prescription, which will be sent back to the system. The reporting device (24) will then print a test report, a prescription and/or sales receipt to be presented to the customer. The customer may also pick up the eyewear from the 3D printer and/or the eyewear dispensing station when it is ready.

In some embodiments, the system of the present invention is capable of creating eye glasses or contact lenses that can modify a person's vision and create a custom prescription that goes beyond what a normal human sees. For example, the system (10) can create eye glasses or contact lenses that allow a person to see in a different spectrum, e.g., the infrared spectrum, or any other spectra that a normal human eye cannot see. Further, the system of the invention is capable of creating customized eyewear that allows a wearer to see how animals see. For example, the customized eyewear may allow visualization in different environments, such as in water, by allowing the wearer to see black and white, grayscale or monochromatic images. As another example, the eyewear may allow visualization of spectrums not visible to the human eye, such as the ultraviolet patterns on flowers visible to bees. In additional embodiments, the customized eyewear produced by the system (10) allows surgeons to see through opaque fluids, such as blood, milk, etc.

This is achieved by coating the lenses during or after the 3D printing to adjust the image spectra. The 3D printer is also capable of printing a stack of lenses which are then fused together to optimize color spectrums by separately coating individual lenses.

Figure 5:
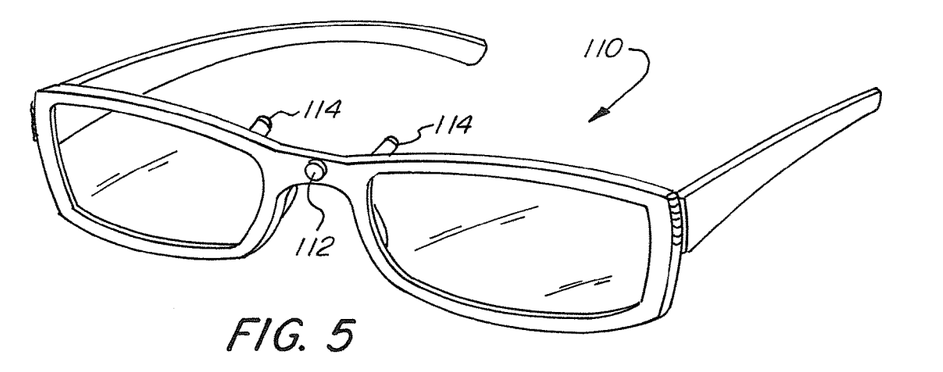
FIG. 5 is a perspective view of a vision correction device produced by the robotic vision screening system of FIG. 4.

In additional embodiments, the system of the present invention (10) creates eyewear (110) that has two or more microcameras, as shown in FIG. 5. One of the microcameras (112) is positioned such that it looks out into the surroundings. This microcamera may be positioned in the nose bridge between the lenses, on one or both sides of the glasses, or at any other suitable location. The other microcamera (114) is positioned such that it looks into one or both of the wearer's eyes to track the movement of the eye. Any suitable type of microcamera may be used. The imaging data obtained by the cameras (112, 114) is then transmitted through a wired connection or wirelessly to a remote location for processing and display to a user.

One of the applications for such eyewear is in warfare. For example, the eyewear (110) will allow people to visualize and monitor exactly what a soldier sees and does not see in a battlefield. Then, the soldier may be warned to look at potential threats that may not be in his or her current field of view. Another application is in consumer studies. For example, a consumer may be wearing the eyewear with the cameras/sensors that allow one to monitor and see what products/marketing material the consumer is more attracted to and spends more time looking at.

The system of the present invention coordinates a person's individual eye sight prescription measured by the diagnostic devices with the sensors/cameras (112, 114) positioned on the eyewear (110). This allows for visualizing/monitoring exactly what each individual sees. For example, if a person is nearsighted, the system will process the image obtained by the cameras positioned on the eyewear and will adjust that image based on the person's degree of nearsightedness to produce an image that that person actually sees.

Figure 6:
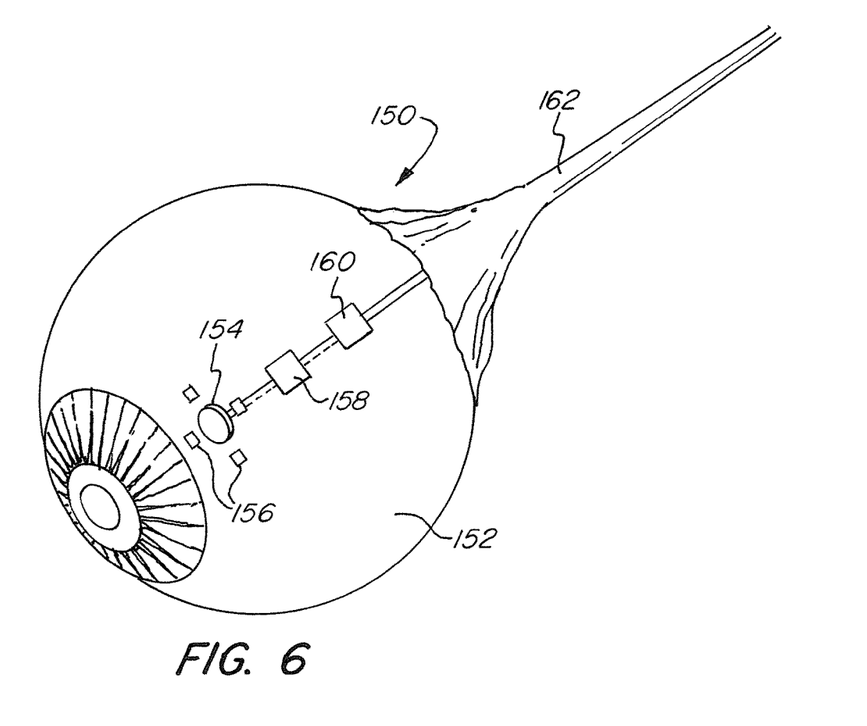
FIG. 6 is a partially schematic view of an artificial eye produced by the robotic vision screening system of FIG. 4.

In further embodiments, the system (10) of the present invention is capable of creating an artificial eye, as shown in FIG. 6. The robotic eye (150) may be created on the spot by the 3D printer based on various data received from the diagnostic devices and/or the measurement devices. Alternatively, the collected data may be transmitted to a remotely located manufacturer for production of the customized robotic eye to be dispensed to the customer. The robotic eye (150) includes a robotic eye ball (152) that mimics a human eye ball. The robotic eye (150) further includes a camera or an imaging sensor (154) that captures an image to be transmitted to the person's brain. One or more illumination devices (156) are positioned adjacent the camera (156) to provide illumination. In some advantageous embodiments, the camera (154) is mounted on a system that acts like real muscles inside a human eye, allowing the camera to mimic the delicate movements of the eye. Any type of suitable material such as e.g. piezoelectric materials or elastic ceramics, may be used for the movement system.

The robotic eye further includes a central control unit (CCU) and a central processing unit (CPU) coupled to the camera (154). The CCU is used to control the movement of the camera to produce an image. The CPU processes the imaging data captured by the camera and converts it into visual information in the form of electronic signals that are transmitted to the optic nerve (162), which is fluidly connected to the CPU. The visual information then moves to the brain, where it is translated into patterns of light that can take the shape of objects, thereby allowing a person to see the objects. The robotic eye (150) also includes a power source for powering the components of the eye. It is understood that the robotic eye may have any other suitable structure/components.

The system of the present invention may be placed in an optometrist office or any other public place, e.g. pharmacy or supermarket, to provide a fully or at least partially automated very comprehensive eye test and measurement system, and also having a point-of-purchase capability where a customer may obtain a highly customized eyewear product on the spot. The system of the present invention provides an advantage in that optometrists and ophthalmologists would no longer have to carry a large inventory of lenses and glasses to accommodate the patient's need. Instead, customized glasses or lenses may be prepared on the spot by the present system. The system of the present invention is also capable of creating various types of unconventional clinical eyewear that is geared towards each patient's unique anatomy and needs. For example, the system may create glasses that sit on a bridge of the patient's nose and do not have earpieces to accommodate patient's that cannot tolerate pressure on the temples, etc.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A robotic vision screening system, comprising:
   a user interface that interacts with a customer;
   at least one camera that examines at least one of the customer's eyes;
   at least one measurement device that measures the customer's head anatomy, wherein the at least one measurement device also measures movement of the customer's eyes during the examination of the customer's eyes and adjusts the positioning of the at least one camera performing the examination in relation to the eyes based at least in part on the measured movement;
   a processor in communication with the at least one camera and the at least one measurement device; and
   a 3D printer in communication with the processor that produces a customized vision correction device based on data received from the at least one camera and the at least one measurement device.

2. The robotic vision screening system of claim 1, wherein the customized eye vision correction device comprises eye glasses.

3. The robotic vision screening system of claim 1, wherein the customized eye vision correction device comprises contact lenses.

4. The robotic vision screening system of claim 1, wherein the customized eye vision correction device comprises an artificial eye.

5. The robotic vision screening system of claim 1, wherein the at least one measurement device comprises a laser scanning device.

6. The robotic vision screening system of claim 1, wherein the at least one measurement device measures at least one of a head measurement, a brow measurement, an eye measurement, an ear measurement, a nose measurement, and a cheek measurement.

7. The robotic vision screening system of claim 1, wherein the processor creates a 3D model of the customer's head based on the measurements received from the at least one measurement device.

8. The robotic vision screening system of claim 7, further comprising a display, wherein the display displays the 3D model of the customer's head to the customer.

9. The robotic vision screening system of claim 8, further comprising a menu of vision correction devices selectable by the customer, wherein the menu includes at least one of a style, color, size and dimension.

10. The robotic vision screening system of claim 9, wherein the display displays a vision correction device selected by the customer together with the 3D model of the customer's head.

11. The robotic vision screening system of claim 9, wherein the 3D printer produces a vision correction device that is customized based on the customer's input from the menu.

12. The robotic vision screening system of claim 1, wherein the at least one camera comprises at least one camera for visualizing eye anatomy using a visible light spectrum and an invisible light spectrum.

13. The robotic vision screening system of claim 1, further comprising a communication link that communicates with a remotely positioned provider.

14. The robotic vision screening system of claim 1, further comprising a reporting device that issues an examination report and/or a prescription.

15. The robotic vision screening system of claim 1, wherein the 3D printer is configured to print vision correction devices that allow the customer to see different light spectra.

16. The robotic vision screening system of claim 1, wherein the customized vision correction device produced by the system comprises a first microcamera and a second microcamera, wherein the first microcamera is configured to visualize a wearer's eye, and the second microcamera is configured to visualize the wearer's surroundings, such that the first and second microcameras produce an image of what the wearer sees when wearing the device, and wherein both first and second microcameras are positioned on the vision correction device.

17. The robotic vision screening system of claim 16, wherein the customized vision correction device produced by the system further comprises a transmitting device that transmits the image of what the wearer sees when wearing the device to a remote location.

18. A method for robotic vision screening, comprising the steps of:
providing a user interface for interaction with a customer;
examining at least one of a customer's eyes via at least one camera;
measuring the customer's head anatomy via at least one measurement device;
measuring movement of the customer's eyes via the at least one measurement device during the examination of the customer's eyes and adjusting positioning of the at least one camera performing the examination in relation to the eyes based at least in part on the measured movement;
processing data obtained by the at least one camera and the at least one measurement device via a processor; and
producing a customized vision correction device via a 3D printer based on the processed data and dispensing the device to the customer.

19. The method for robotic vision screening according to claim 18, wherein the customized eye vision correction device comprises eye glasses.

20. The method for robotic vision screening according to claim 18 wherein the customized eye vision correction device comprises contact lenses.

21. The method for robotic vision screening according to claim 18, wherein the customized eye vision correction device comprises an artificial eye.

22. The method for robotic vision screening according to claim 18, wherein the customer's head anatomy is measured via a laser scanning device.

23. The method for robotic vision screening according to claim 18, further comprising the steps of creating a 3D model of the customer's head based on the measurements received from the at least one measurement device and displaying the 3D model of the customer's head to the customer via a display.

24. The method for robotic vision screening according to claim 18, wherein the step of producing the customized vision correction device comprises producing a vision correction device comprising a first microcamera and a second microcamera, wherein the first microcamera is configured to visualize a wearer's eye, and the second microcamera is configured to visualize the wearer's surroundings, such that the first and second microcameras produce an image of what the wearer sees when wearing the device, and wherein both first and second microcameras are positioned on the vision correction device.

25. The method for robotic vision screening according to claim 24, further comprising the step of transmitting the image of what the wearer sees when wearing the device to a remote location.

* * * * *